(12) United States Patent
Gu et al.

(10) Patent No.: US 6,280,443 B1
(45) Date of Patent: Aug. 28, 2001

(54) SPINAL FIXATION SYSTEM

(76) Inventors: Ja-Kyo Gu, 17-611, Sangah Apt., 505 Junggye-dong, Nowon-gu, Seoul (KR), 139-220; Howard S. An, 1725 W. Harrison St., Suite 1063, Chicago, IL (US) 60612; Tae-Hong Lim, 3619 Othello Dr., Naperville, IL (US) 60564

( * ) Notice: Subject to any disclaimer, the term of this patent is extended or adjusted under 35 U.S.C. 154(b) by 0 days.

(21) Appl. No.: 09/442,766

(22) Filed: Nov. 18, 1999

(30) Foreign Application Priority Data

Jan. 30, 1999 (KR) .................................................. 99-3161

(51) Int. Cl.⁷ .................................................. A61B 17/56
(52) U.S. Cl. .................................................. 606/61
(58) Field of Search ........................... 606/60, 61, 53, 606/86, 72, 73

(56) References Cited

U.S. PATENT DOCUMENTS

| | | | |
|---|---|---|---|
| 5,053,034 | * 10/1991 | Olerud | 606/61 |
| 5,254,118 | * 10/1993 | Mirkovic | 606/61 |
| 5,312,404 | * 5/1994 | Asher et al. | 606/61 |
| 5,474,551 | * 12/1995 | Finn et al. | 606/61 |
| 5,476,463 | * 12/1995 | Boachie-Adjei et al. | 606/61 |
| 5,487,744 | * 1/1996 | Howland | 606/61 |
| 5,569,247 | * 10/1996 | Morrison | 606/61 |
| 6,083,226 | * 7/2000 | Fiz | 606/61 |

\* cited by examiner

*Primary Examiner*—Gene Mancene
*Assistant Examiner*—Eduardo C. Robert
(74) *Attorney, Agent, or Firm*—Reed Smith Hazel & Thomas LLP

(57) ABSTRACT

A spinal fixation system for use in the immobilization of a sequence of spinal bones, comprising a plurality of pedicle screws, a pair of rods, and connectors. The pedicle screw has a spherical head having a round portion at an upper portion of the spherical head, a threaded shaft for insertion through the pedicles, and a threaded stem on the top of the spherical head. The connector has a rod passage for receiving the rod therethrough, a set member bore formed in an upper portion of the connector, and a support portion having an opening formed for adapting the stem of the pedicle screw and a recessed hemispherical wall. A spherical joint at the pedicle screw and the connector allows the multi-directional adjustment capability of the connector so that the screws can be implanted in any angulation with no need of having the screws well aligned. The spherical head of the pedicle screw and the hemispherical wall have slightly different diameters which improve the locking power and provide a rigid fixation. A rigid coupling is achieved between the rod and the connector by making the cross-section of the rod passage as an imperfect circular shape which allows the three point contact between the rod and the rod passage. The assembly is locked in place by tightening a fixing cap and a set member from the posterior aspect of the spine.

12 Claims, 4 Drawing Sheets

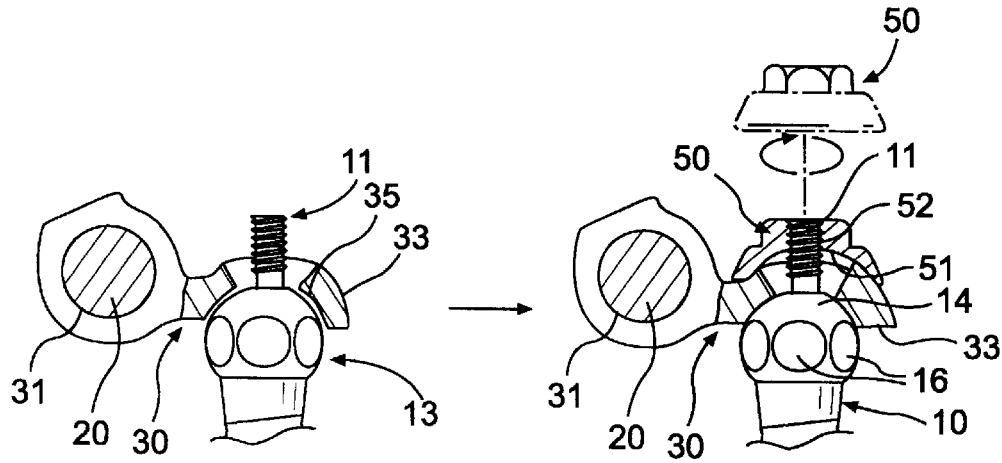
FIG. 4A  FIG. 4B
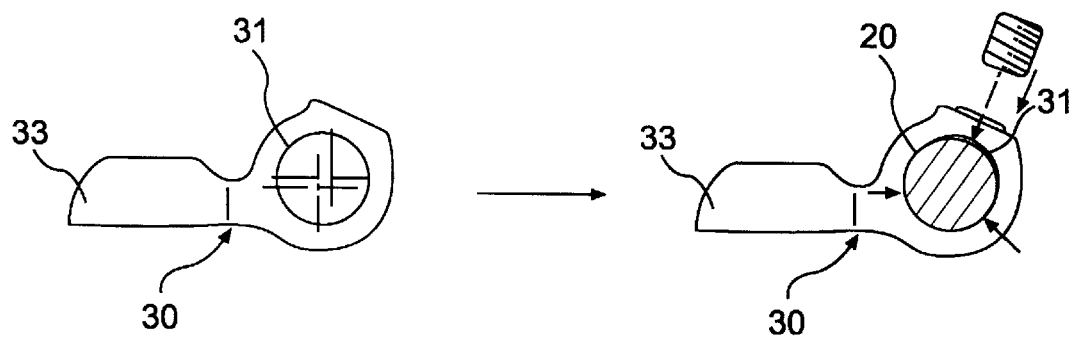
FIG. 5A  FIG. 5B

SPINAL FIXATION SYSTEM

BACKGROUND OF THE INVENTION

1. Field of the Invention

The present invention generally relates to a spinal fixation system for use in the immobilization of a sequence of spinal bones. More particularly, the present invention relates to a spinal fixation system which allow the implantation of the pedicle screws at the best anatomic location and orientation with flexibility of screw placement and alignment; easy and simple connection between the rod and the screws without application of excessive force to the spine and/or implants during assembly; the top-tightening mechanism to lock the assembly in place with better visibility and access to the spine and implants; a rigid segmental fixation for enhanced maintenance of correction and solid fusion process; and a low profile of the assembly.

2. Description of the Prior art

The human spine is a complex columnar structure of vertebral bone and connective tissues. The vertebrae, discs, and ligaments are intricately arranged, and the complex interaction amongst these structures provides flexibility for motion, spinal cord protection and distribution of body forces. In the diseased or injured state, this delicate equilibriums disturbed and results in spinal pathologies. In many cases, the spinal disorders can be treated by a conservative nonsurgical methods, such as medication, exercise and physical therapies. However, some spinal disorders, such as degenerative instability, deformity, trauma, and tumors, require a surgical intervention to treat pain induced by nerve root compression and unstable invertebral joints.

The surgical procedures for the thoracolumbar spine involves the dissection of soft tissues and often the removal of load bearing structures, such as vertebral bone and discs to decompress the neural elements. Such decompression procedures lead to spinal instability and it is often necessary to fuse spinal segment to restore the stability. Internal fixation with instrumentation accompanies surgical fusion to augment the bony fusion by achieving temporary but rigid fixation that provides a stable environment for bone fusion as well as a maintenance of corrected alignment of the spine.

A variety of internal spinal fixation systems have been developed and used in spine surgery to achieve such a rigid fixation by implanting artificial assemblies in or on the spine. Spinal implants can be classified as anterior or posterior instrumentation systems based upon the implanting location. Anterior implants are coupled to the anterior portion of the spine. The use of posterior implants using pedicle screws coupled by longitudinal rods has become more popular because of their capability of achieving a rigid fixation. Such posterior implants generally comprise pairs of rods, which are aligned along the longitudinal axis of the spine, and which are then attached to the spinal column by screws which are inserted through the pedicles into respective vertebral bodies.

The surgical procedure to achieve a posterior fixation using pedicle screws and connecting rods generally includes the insertion of screws into pedicles in a predetermined angle and depth, temporary coupling of the rods to the screws, the proper correction of spinal curve, and the secure connection of rods to the screws for rigid fixation. A considerable difficulty identified in this surgical procedure is associated with the coupling of a rod to a plurality of screws that are not well aligned in general because the angle and depth of the screw insertion should be determined by patient' anatomical and pathological conditions that may vary among spinal levels as well as among patients. It has been identified that attempts for addressing such a difficulty result in the application of unnecessarily excessive loads to the spinal column via the pedicle screws and the increased operation time, which are known to cause many complications associated with surgery.

For successful posterior spinal instrumentation, it is essential to securely mount the screws and the rods on the spinal column without applying unnecessary forces to the spine and the implants which may cause an acute or fatigue failure of the surgical construct. A variety of attempts have been made to address this issue. Such attempts can be classified into two methods. The first method is the use of a connector comprising a hole to adapt a rod at one end and an oblong hole used for coupling with screws at the other end (ISOLA® Spinal System, Acromed Corporation, Clevelan, Ohio). This connector permits some freedom with respect to the distance between the rod and screw axes by the use of an oblong hole, but not with respect to angulation of the screw and the coupling element. A variety of washers with a declined surface at various angles are used to obtain some freedom with respect to angulation in coupling the angulated screws and the rod. However, the selection and use of various washers in as proper manner is a tedious manipulation of many small parts during surgery in which there should be extreme limitations in terms of time and space. The use of washers also elevates the profile of the assembly, which causes patients' discomfort and often results in additional surgery for removal of the implants. The other method is the use of polyaxial screws that permits freedom with respect to angulation of the screw. The use of polyaxial screws, however, generally has difficulties in coupling the screw with the rod located apart from the screw head. An example of a polyaxial pedicle screw having a through bar clamp locking mechanism is disclosed in U.S. Pat. No. 5,961,518 to Errico et al., issued Oct. 5, 1999. Such polyaxial pedicle includes a pedicle screw and coupling element assembly which provides a polyaxial freedom of implantation angulation with respect to rod reception, and which comprises a reduced number of elements and thus correspondingly provides for expeditious implantation. In this invention, however, the screw and rod assembly should be locked using a nut oriented sideways (i.e., the tightening nut faces the lateral side of the patient during surgery), which is very inconvenient to perform in a very limited lateral operating space. In fact, most surgeons prefer the top-tightening mechanism (i.e., the axis of tightening member faces the posterior side of the patient) because the top-tightening mechanism provides better visibility and access than the side-tightening mechanism. Polyaxial couplings of the screw and the rod used in previous inventions are also not likely to provide either sufficient joint-locking power to prevent the slippage and rotation of the screw with respect to the rod or the polyaxial freedom of implantation angulation. The sufficient locking power in couplings is required to achieve a rigid fixation to provide a stable environment for successful bony fusion and also to maintain the correction until solid fusion occurs. Freedom i controlling both angulation and distance between the screw and the rod is required not only to reduce the surgery time but also to prevent the application of unnecessary stresses on the implant and the spine which may cause a failure in surgery.

SUMMARY OF THE INVENTION

Therefore, it is in the primary object of the present invention to provide a reliable, top-tightening spinal fixation system comprising pedicle screws, rods, and connecting and tightening members, which provides freedom of implantation not only with respect to angulation of the screw but also with respect to the distance between the screw head and the rod using a reduced number of elements for easy, simple and expeditious implantation.

It is also an object of the present invention to maintain or improve the joint-locking power for achieving a rigid fixation while preserving the freedom of implantation.

In addition, it is another object of the present invention to prevent the application of unnecessary stresses on the implant and the spine which may cause a failure in surgery.

The preceding objects of the invention are achieved by the present invention that is a posterior transpedicular instrumentation system comprising:

a plurality of pedicle screws, each pedicle screw having a spherical head, a threaded shaft for insertion through the pedicles at the bottom of the spherical head, and a threaded stem on the top of the spherical head;

a pair of rods being located in the lateral aspect and connected to the pedicle screws, the rods extending on both sides of the spinous processes along the length of the spinal column for preventing the movement of the injured or decompressed vertebrae;

a number of connectors with various sizes for coupling the pedicle screw with the rod, each connector having a rod passage formed to receive the rod therethrough, a set member bore formed in an upper portion of the connector to intersect perpendicular to the rod passage, and a support portion having an opening formed for adapting the stem of the pedicle screw and a recessed hemispherical wall;

a number of set members, each set member being inserted into the set member bore of the connector for tightening the rod inserted through the rod passage of the connector; and, a number of fixing caps, each fixing cap having a stem bore for tightening the threaded stem of the pedicle screw protruding through the opening in the support portion of the connector.

In more detail, the round portion in the spherical head of the pedicle screw and the recessed hemispherical wall in the support portion of the connector form a spherical joint (with which the connector) and thus the rod can be placed into the required angular position. In the meantime, the use of connectors with different sizes provides lateral adjustment of the rod that can be located at various distances from the pedicle screws because of anatomic variations. In addition, the use of the spherical head of the pedicle screw and the hemispherical wall having slightly different diameters improves the locking power and provides a rigid fixation. A similar locking mechanism is employed to achieve a rigid connection of the rod to the connector.

Other objects and benefits of the present invention will become apparent upon consideration of the following written description taken in conjunction with the accompanying figures.

BRIEF DESCRIPTION OF THE DRAWINGS

FIG. 4A is a front view illustrating that the connector is imperfectly matched to a round surface of the pedicle screw before a fixing cap is engaged to a stem of the pedicle screw; and FIG. 4B shows that the connector is perfectly matched to the round portion surface of the pedicle screw by engaging the fixing cap to the stem.

FIG. 5A is a front sectional view illustrating a rod passage which is made to have an outer boundary of two circles of slightly different diameters located at slightly eccentric center positions; and FIG. 5B shows that the rod passage is matched with the rod by a set member.

DETAILED DESCRIPTION OF THE PREFERRED EMBODIMENTS

Figure 1:
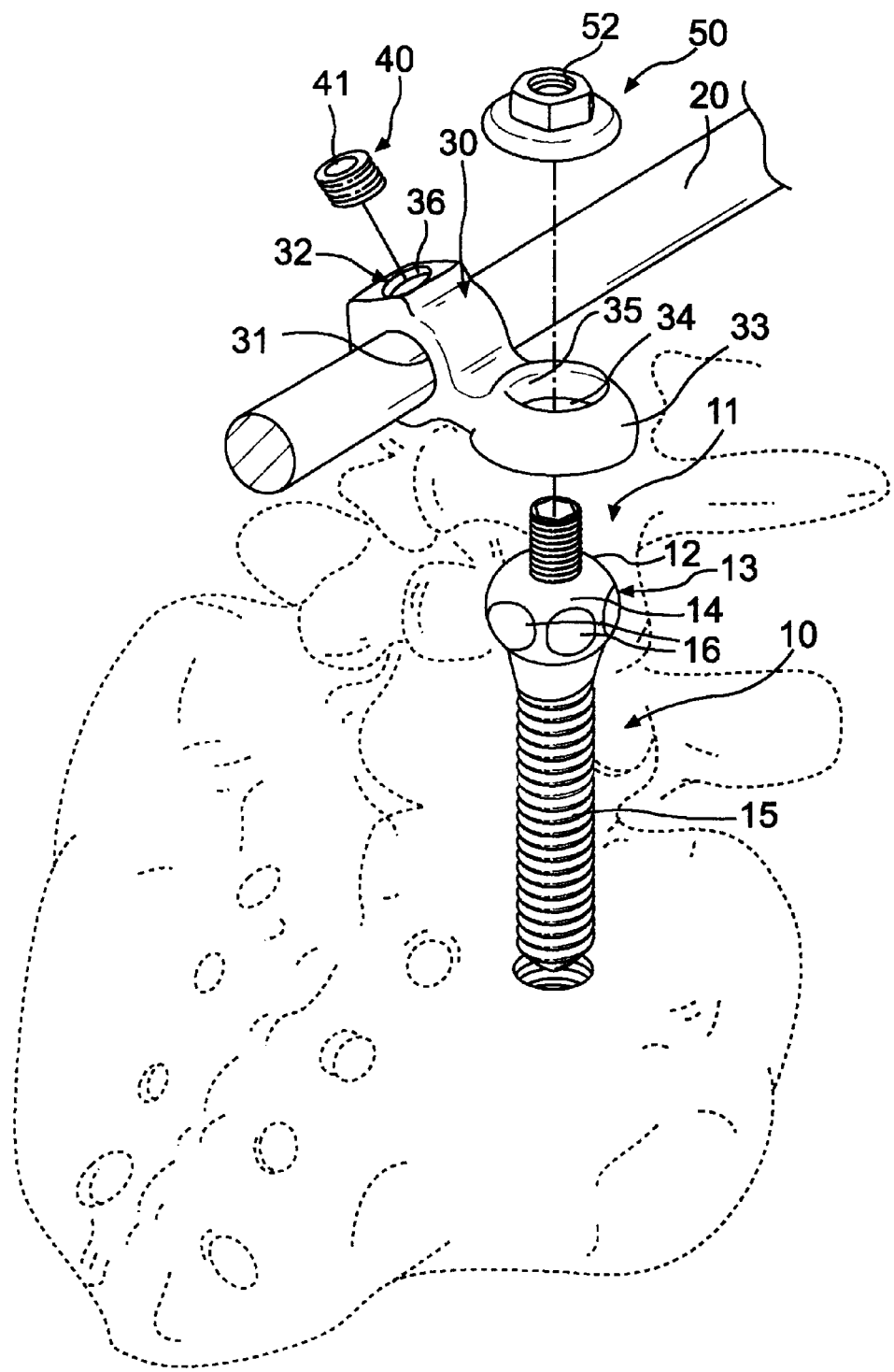
FIG. 1 is an exploded perspective view of a spinal fixation system of the present invention.

The present invention will be described in detail hereinafter with reference to the accompanying drawings, wherein same reference characters designate corresponding parts throughout several views. It is understood to be that these drawings depict only typical embodiments of the invention and are, therefore, not to be considered limiting of its scope.

Referring now to FIG. 1, a pedicle screw 10 to be implanted into a selected pedicle of the patient's vertebrae comprises a stem 11 protruded from a top portion thereof, a spherical head 13 formed below the stem 11, and a threaded shaft 15. The stem 11 has threads 12 on its outer surface. The spherical head 13 has six cut portions 16 along its equator line so as to make a hexagonal shape in its middle portion for inserting the pedicle screw 10 using a spanner, wrench or the likes. A round portion 14 is the upper portion of the spherical head 13, which serves as a part of ball and socket joint between the pedicle screw 10 and a connector 30 which will be described below. The shaft 15 of the pedicle screw 10, although shown to be like a bolt in FIG. 1, is used for being anchored into and holding the vertebra and will be, therefore, able to have any type of threads which is adequate for securely holding the bone.

The connector 30 in FIG. 1, which connects a rod 20 to the pedicle screw 10 comprises a rod reception portion on one end and a screw reception portion on the other end.

The rod reception portion of the connector 30 has a rod passage 31 to receive the rod 20 therethrough and a set member bore 32 formed in an upper portion of the rod reception portion of the connector 30 and intersecting perpendicular to the rod passage 31. The surface of the set member above 32 is threaded to be engaged with a set member 40 which has a threaded outer surface for secure tightening of the rod 20 to the connector 30.

The set member 40 has a recess 41 (See FIG. 1) of hexagonal cross-section for insertion into the set member bore using an allen wrench. The length of the set member should be short enough not to protrude from the upper surface of the set member bore 32 of the connector 30 to lower the profile of the complete assembly.

The screw reception portion of the connector 30 comprises a support portion 33 of a hemispherical shape which has an opening 34 formed to receive the stem 11 of the pedicle screw 10 and a recessed hemispherical wall 35 therein. The diameter of the recessed hemispherical wall 35 is slightly less than that of the round portion 14 of the upper portion of the spherical head 13. The stem 11 of the pedicle screw 10 which extends through the opening 34 is engaged to a fixing cap 50.

The fixing cap 50 in FIG. 1 comprises a stem bore 52 which is a threaded hold formed to engage the stem 11 of the pedicle screw 10 and a recessed spherical bottom surface 51 formed to be hollowed inside its surface thereof.

Figure 2:
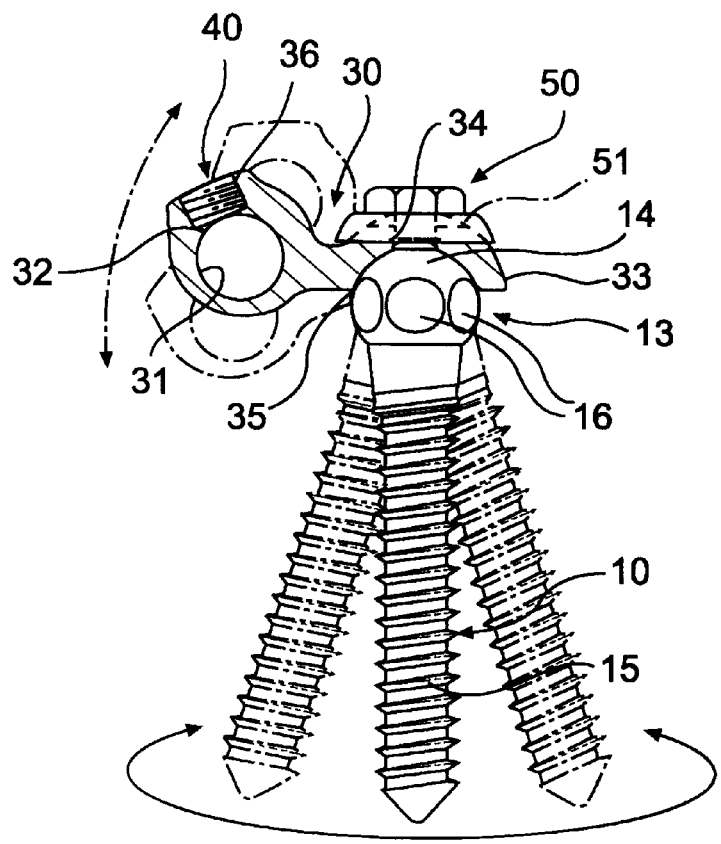
FIG. 2 is a front sectional view illustrating a pedicle screw and a connector which are polyaxially engaged regardless of the insertion angle of a pedicle screws.
Figure 3:
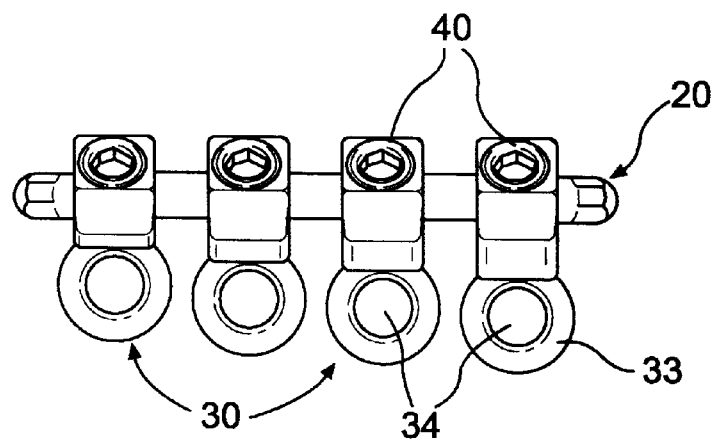
FIG. 3 is a plan view of the connectors with various sizes for coupling the pedicle screw to a rod with lateral adjustment.

As depicted in FIG. 2, the round portion 14 formed at the upper portion of the pedicle screw 10 is held in the recessed hemispherical wall 35 of the opening 34 during assembly. The round portion 14 of the pedicle screw 10 and the recessed hemispherical wall 35 of the support portion 33 of the connector 30 are formed in almost the same spherical surfaces. Thus, the connector 30 is freely rotated with respect to the pedicle screw 10 before tightening, and thus the pedicle screw 10 and the connector 30 are polyaxially engaged regardless of the insertion angle of the pedicle screw 10. In addition to this polyaxial adjustability, the use of the connector 20 with different distances between the rod and screw reception portions provides the capability for lateral adjustment in controlling the rod position (See FIG. 3). These features allow easy coupling of the rod 20 to the pedicle screw 20 using the connector 30 in all directions.

Figure 6:
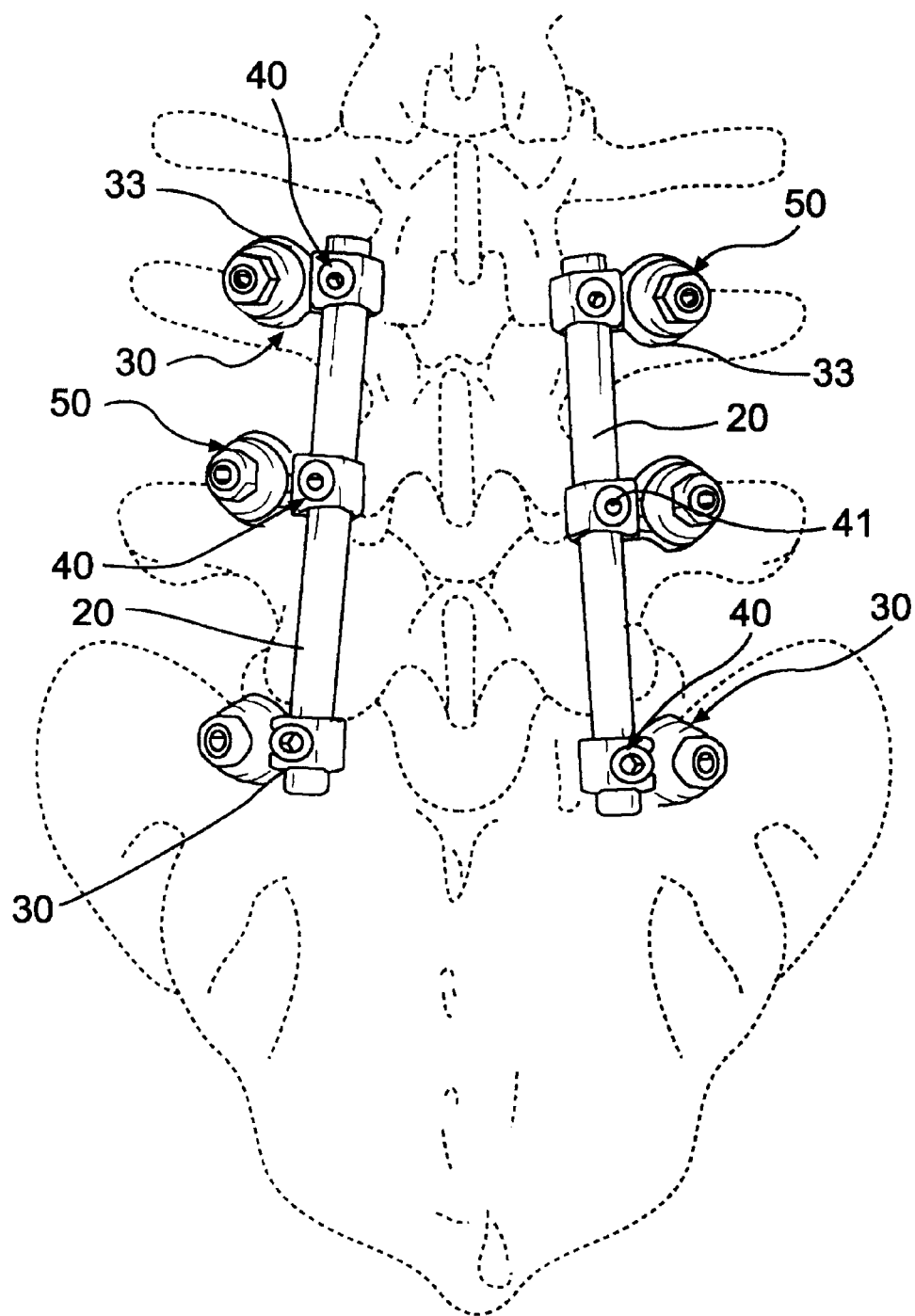
FIG. 6 is a top elevational view illustrating a state that this fixation device is implanted in the spinal column.

After complete engagement of the rod 20 to the pedicle screw 10 using the connector 30, a firm fixation between the pedicle screw 10 and the connector 30 is achieved by tightening the fixing cap 50, and a firm fixation between the rod 20 and the connector 30 is achieved by tightening the set member 40. It should be noted that, in both cases, the assembly can be locked in place from the posterior aspect of the spine (top-tightening) as shown in FIG. 6. This top-tightening procedure allows a simple locking mechanism that provides better visibility and access than side-tightening/locking mechanism.

Additional unique features of the present invention are associated with the mechanism to obtain a rigid connection between the pedicle screw 10 and the rod 20 using the connector 30. Referring to FIG. 4, the diameter of the round portion 14 of the pedicle screw 10 is a little larger in fine tolerance than that of the inner hemispherical wall 35 of the connector 30. When the fixing cap 50 is engaged to the stem 11 of the pedicle screw 10 which extends through the opening 34 of the support portion 33 and tightened, an imperfectly matched surface contact occurs while maintaining the position and orientation of the connector 30 with respect to the screw 10 and the rod 20 in place. Such a ball-and-socket like connection with imperfectly matched surface contact provides an improved prevention of slippage within the joint compared with a conventional ball and socket joint with a perfectly matched surface contact. In addition, such an imperfectly matched surface contact induces the deformation of the support portion 33 of the hemispherical shell shape when the fixing cap 50 is tightened. The deformed support portion 33 of the connector 30 made of an elastic titanium alloy tends to return back to the original shape, which pushes the fixing cap 50. This elastic (or springback) force prevents loosening of the fixing cap 50, which eliminates the use of an additional nut which has been used in previous spinal fixation systems in order to prevent loosening.

A similar method is used to improve the strength of the rod 20 and connector 30 fixation. As shown in FIG. 5, the cross section of the rod passage 31 is made to have an outer boundary of two circles of slightly different diameters located at a slightly eccentric center positions so as to form a hole of imperfect-circular cross-section. When the rod 20 is compressed by the set number 40 for fixation, this provides at least a three point contact between the rod 20 and the rod passage 31 regardless of the rod bending status, which prevents the rotation and slippage of the connector 30 with respect to the rod 30 more effectively.

The implantation procedure of the present invention to achieve the surgical construct as shown in FIG. 6 is described hereafter. The pedicle screw 10 is inserted into the pedicle according to the best anatomic location and orientation at each spinal level without considering the alignment of screws for later attachment of the rod to the pedicle screws. The rod 20 is engaged to the connector 30 through the rod passage 31 and temporarily nested in the rod passage 31 by applying a small compressive load using the set member 40. Then, the rod-connector 30 allows the location of the rod 20 lateral to the pedicle screw 10, which lowers the profile of the present invention significantly. The variability in screw placement and screw-rod connection achieved in the present invention allows a physician to implant the screw according to the best anatomic location and orientation with no need for considering the alignment of the pedicle screws. These features also minimize the need for precise bending of the rod 20 which has been required for the implantation of some spinal fixation systems which do not have such variability in screw-rod connection.

Those skilled in the art will readily recognize that these and various other modifications and changes may be made to the present invention without strictly following the exemplary application illustrated and described herein and without departing from the true spirit and scope of the present invention, which is set forth in the following claims.

What is claimed is:

1. A spinal fixation system for fixing at least one injured or decompressed vertebrae to a spine comprising:

a plurality of pedicle screws, each pedicle screw having a stem protruding from a top portion thereof, the stem having threads on its outer surface, a spherical head formed below the stem, and a threaded shaft which is insertable to a pedicle of the vertebrae;

a pair of rods for being located in a lateral aspect of the spine and connected to the pedicle screws, the rods extending are capable of on both sides of a plurality of spinal processes of the spine along the length of the spine for preventing a movement of the vertebrae;

a number of correctors for coupling each of the pedicle screws to the rods with lateral adjustment, each connector having a rod passage formed to receive the rod therethrough, a set member bore formed in an upper portion of the connector to intersect perpendicular to the rod passage, and a support portion of a hemispherical shell which provides rotational freedom in coupling the pedicle screw and the connector, the support portion having an opening formed through a middle part of the support portion for holding the stem of the pedicle screw and a recessed hemispherical wall therein;

a number of set members, each set member being inserted into the set member bore of the connector for fastening the rod inserted in the rod passage of the connector; and a number of fixing caps, each fixing cap having a stem bore formed to adapt the stem of the pedicle screw therethrough and a recessed hemispherical bottom surface, wherein the rod passage is made to have an outer boundary of two circles of slightly different diameters located at slightly eccentric center positions, and wherein at least a three point contact occurs between the rod and the rod passage by tightening the fixing cap regardless a degree to which the rod is bent.

2. The spinal fixation system set forth in claim 1, wherein the spherical head has six cut portions along its equator line so as to make a hexagonal shape in its middle portion.

3. The spinal fixation system set forth in claim 1, wherein the spherical head has a round portion at its upper portion, the round portion serving as a part of ball and socket joint between the pedicle screw and the connector.

4. The spinal fixation system set forth in claim 3, wherein the round portion is formed in significantly the same as a spherical surface of the recessed hemispherical wall of the support portion of the connector, so that the connector is rotated with respect to the pedicle screw in all directions before tightening.

5. The spinal fixation system set forth in claim 1, wherein the se member has a threaded outer surface for securely tightening the rod to the connector and a recess of hexagonal cross-section formed at a top portion thereof.

6. The spinal fixation system set forth in claim 1, wherein the set member has a length being short enough not to protrude from an upper surface of the set member bore of the connector so as to lower a profile of the complete assembly.

7. The spinal fixation system set forth in claim 1, wherein the set member bore of the connector is threaded on its inner surface to be engaged with the set member.

8. The spinal fixation system set forth in claim 1, wherein the connector is made of titanium alloy with elastic force and tends to return back to an original shape.

9. The spinal fixation systems set forth in claim 1, wherein each of the connectors has different distances between the rod passage and the support portion thereof to provide the capability for lateral adjustment in controlling the rod position.

10. The spinal fixation system set forth in claim 1, wherein the fixing cap and the set member tighten the spinal fixation system to the posterior aspect of the spine.

11. The spinal fixation system for fixing at least one injured or decompressed vertebrae to a spine comprising:

- a plurality of pedicle screws, each pedicle screw having a stem protruding from a top portion thereof, the stem having threads on its outer surface, a spherical head formed below the stem, and a threaded shaft which is inserted to a pedicle of the vertebrae;
- a pair of rods being located in a lateral aspect of the spine and connected to the pedicle screws, the rods extending on both sides of a plurality of spinal processes of the spine along the length of the spine for preventing a movement of the vertebrae;
- a number of correctors for coupling each of the pedicle screws to the rods with lateral adjustment, each connector having a rod passage formed to receive the rod therethrough, a set member bore formed in an upper portion of the connector to intersect perpendicular to the rod passage, and a support portion of a hemispherical shell which provides rotational freedom in coupling the pedicle screw and the connector, the support portion having an opening formed through a middle part of the support portion for holding the stem of the pedicle screw and a recessed hemispherical wall therein;
- a number of set members, each set member being inserted into the set member bore of the connector for fastening the rod inserted in the rod passage of the connector; and
- a number of fixing caps, each fixing cap having a stem bore formed to adapt the stem of the pedicle screw therethrough and a recessed hemispherical bottom surface,
- wherein the spherical head has a round portion at its upper portion, the round portion serving as a part of ball and socket joint between the pedicle screw and the connector, and
- a diameter of the round portion of the pedicle screw is a larger in fine tolerance than that of the inner hemispherical wall of the connector so that an imperfectly matched surface contact between the pedicle screw and the connector occurs, and wherein the imperfectly matched surface contact induces a deformation of the support portion of the hemispherical shell shape when the fixing cap is tightened, and provides a firm fixation between the pedicle screw and the connector.

12. The spinal fixation system set forth in claim 11, wherein the fixing cap and the set member tighten the spinal fixation system to the posterior aspect of the spine.

* * * * *